(12) United States Patent
Takemoto et al.

(10) Patent No.: US 10,827,993 B2
(45) Date of Patent: Nov. 10, 2020

(54) X-RAY APPARATUS FOR ROUNDS

(71) Applicant: Shimadzu Corporation, Kyoto (JP)

(72) Inventors: Hajime Takemoto, Kyoto (JP); Toru Hayakawa, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/479,159

(22) PCT Filed: Jan. 18, 2017

(86) PCT No.: PCT/JP2017/001597
§ 371 (c)(1),
(2) Date: Jul. 18, 2019

(87) PCT Pub. No.: WO2018/134923
PCT Pub. Date: Jul. 26, 2018

(65) Prior Publication Data
US 2020/0037970 A1 Feb. 6, 2020

(51) Int. Cl.
*H05G 1/02* (2006.01)
*A61B 6/00* (2006.01)
*A61B 90/50* (2016.01)

(52) U.S. Cl.
CPC .............. *A61B 6/4405* (2013.01); *A61B 6/40* (2013.01); *A61B 90/50* (2016.02)

(58) Field of Classification Search
CPC ......... A61B 6/4405; A61B 90/50; A61B 6/40; A61B 6/447
See application file for complete search history.

(56) References Cited

U.S. PATENT DOCUMENTS 5,283,823 A * 2/1994 Morris ................. A61B 6/4405
378/193
9,521,984 B2 12/2016 Moreno Vallejo et al.
RE47,581 E * 8/2019 Moreno Vallejo ... A61B 6/4405
(Continued)

FOREIGN PATENT DOCUMENTS

| JP | 2004-033415 A | 2/2004 |
| JP | 2016-526425 A | 9/2016 |
| WO | 2017/149672 A1 | 9/2017 |

OTHER PUBLICATIONS

Written Opinion by the International Search Authority for PCT application PCT/JP2017/001597, submitted with a machine translation.

*Primary Examiner* — Kiho Kim
(74) *Attorney, Agent, or Firm* — Muir Patent Law, PLLC

(57) ABSTRACT

This X-ray apparatus for rounds includes an X-ray generator capable of moving up and down in a vertical direction, a holding frame that holds a compression spring or a tension spring that expands and contracts as the X-ray generator moves up and down such that the compression spring or the tension spring is expandable and contractable, that holds a wire rope that transmits an elastic force of the compression spring or the tension spring to the X-ray generator and a pulley around which the wire rope is wound and which rotates, and that supports the X-ray generator such that the X-ray generator is movable up and down, and a support column that extends in the vertical direction and houses the holding frame such that the holding frame is detachable and upwardly exposable.

10 Claims, 10 Drawing Sheets

(56) References Cited

U.S. PATENT DOCUMENTS

| | | | |
|---|---|---|---|
| 2010/0091942 A1* | 4/2010 | Pohjoispuro | A61B 6/14 378/38 |
| 2011/0249805 A1* | 10/2011 | Kralles | A61B 6/4482 378/198 |
| 2012/0224673 A1* | 9/2012 | Barker | A61B 6/4405 378/198 |
| 2014/0098942 A1* | 4/2014 | Omura | H05G 1/02 378/197 |
| 2014/0098943 A1* | 4/2014 | Omura | A61B 6/4452 378/198 |
| 2014/0133627 A1* | 5/2014 | Sakuragi | A61B 6/4429 378/62 |
| 2016/0015342 A1* | 1/2016 | Okuno | A61B 6/105 378/62 |
| 2017/0303882 A1* | 10/2017 | Ficarra | A61B 6/4452 |
| 2018/0242933 A1* | 8/2018 | Sanbuichi | A61B 6/4441 |
| 2019/0069860 A1 | 3/2019 | Takemoto et al. | |
| 2019/0357863 A1* | 11/2019 | Dirisio | A61B 6/447 |

* cited by examiner

[FIRST EMBODIMENT]

FORWARD

FIG.7 [SECOND EMBODIMENT]

[MODIFIED EXAMPLE OF SECOND EMBODIMENT]

X-RAY APPARATUS FOR ROUNDS

TECHNICAL FIELD

The present invention relates to an X-ray apparatus for rounds.

BACKGROUND ART

Conventionally, an X-ray apparatus for rounds that can raise and lower an X-ray generator in a vertical direction is known. Such an X-ray apparatus for rounds is disclosed in Japanese Translation of PCT International Application Publication No. 2016-526425, for example.

Japanese Translation of PCT International Application Publication No. 2016-526425 discloses an X-ray apparatus for rounds including a fixed lower portion having a fixed height, a telescopic support column including a movable upper portion having a variable height, a telescopic arm that moves in a vertical direction along the telescopic support column, and a chassis that supports the telescopic support column. The telescopic arm supports, at its end, a head assembly including an X-ray emitter. The chassis has wheels to transport the equipment.

The X-ray apparatus for rounds disclosed in Japanese Translation of PCT International Application Publication No. 2016-526425 uses a balancing mechanism to balance the weight of the movable portion of the telescopic support column that vertically moves up and down with the weight of a movable suspended body including the telescopic arm so as to fix the movable suspended body at an arbitrary height position. The balancing mechanism includes a tension spring and a pulley fixed to the telescopic support column. The tension spring converts the position gravity energy of the movable suspended body into position elastic energy as the movable suspended body moves up and down. The pulley includes a plurality of pulleys joined to the tension spring, divides a force applied to the tension spring, and multiplies the run of a wire rope (cable) wound around the pulley. Here, in an X-ray apparatus for rounds as disclosed in Japanese Translation of PCT International Application Publication No. 2016-526425, in order to balance the weight of a movable suspended body, a load several to several tens of times the weight of the movable suspended body is applied to a wire rope, and thus after a certain period of use, it is necessary to replace the worn wire rope.

PRIOR ART

Patent Document

Patent Document 1: Japanese Translation of PCT International Application Publication No. 2016-526425

SUMMARY OF THE INVENTION

Problems to be Solved by the Invention

However, in the X-ray apparatus for rounds as disclosed in Japanese Translation of PCT International Application Publication No. 2016-526425, components for balancing the weight of the movable suspended body, such as a tension spring, a pulley, and the wire rope, are directly fixed to a telescopic support column. Therefore, in order to replace the wire rope, it is necessary to disassemble the support column and remove the components from the support column. Such dismantling work is difficult to do in the field (in the hospital), and it is conceivably necessary to bring it back to the factory for replacement work. Thus, the X-ray apparatus for rounds as disclosed in Japanese Translation of PCT International Application Publication No. 2016-526425 has a problem that the workability of wire rope replacement is poor.

The present invention has been proposed in order to solve the aforementioned problems, and an object of the present invention is to provide an X-ray apparatus for rounds in which the workability of wire rope replacement can be improved.

Means for Solving the Problems

In order to attain the aforementioned object, an X-ray apparatus for rounds according to a first aspect of the present invention includes an X-ray generator including an X-ray source that irradiates a subject with X-rays, and capable of moving up and down in a vertical direction, a holding unit that holds a spring member that expands and contracts as the X-ray generator moves up and down such that the spring member is expandable and contractable, that holds a wire rope that transmits an elastic force of the spring member to the X-ray generator and a fixed pulley around which the wire rope is wound and which rotates, and that supports the X-ray generator such that the X-ray generator is movable up and down, and a support column that extends in the vertical direction and houses the holding unit such that the holding unit is detachable and upwardly exposable.

In the X-ray apparatus for rounds according to the first aspect of the present invention, as described above, the holding unit that holds the wire rope is housed in the support column that extends in the vertical direction such that the holding unit is detachable and upwardly exposable. Accordingly, the holding unit that holds the wire rope is moved upward of the support column such that the holding unit can be easily exposed from the support column. Therefore, the wire rope held by the holding unit can be replaced without disassembling the support column, and thus the workability of wire rope replacement can be improved. Moreover, even in the field, wire rope replacement can be performed, and thus it is possible to prevent prolongation of a period during which the X-ray apparatus for rounds cannot be used due to taking the wire rope back to the factory for wire rope replacement.

In the aforementioned X-ray apparatus for rounds according to the first aspect, the wire rope is preferably held in an upper portion of the holding unit, and the holding unit is preferably detached from the support column and moved upward of the support column so as to be exposed from the support column. According to this structure, the wire rope can be replaced by moving the holding unit upward until the upper portion of the holding unit is exposed from the support column, and thus as compared with the case in which the holding unit is moved upward until the entire holding unit is exposed from the support column, the height to which the holding unit is moved upward can be reduced, and the wire rope can be replaced even when the ceiling is low. Consequently, the wire rope can be replaced more easily.

In the aforementioned X-ray apparatus for rounds according to the first aspect, the holding unit preferably further holds a moving pulley around which the wire rope is wound and which moves up and down as the spring member expands and contracts, and the wire rope, the fixed pulley, and the moving pulley are preferably held in an upper portion of the holding unit, and the spring member is preferably held in a lower portion of the holding unit.

According to this structure, the wire rope can be easily removed from the moving pulley and the fixed pulley by moving the holding unit upward until the upper portion of the holding unit is exposed from the support column. Consequently, the wire rope can be replaced more easily.

In the aforementioned structure in which the holding unit holds the moving pulley, the holding unit preferably has a frame shape including an upper surface portion to which the wire rope is fixed, a bottom surface portion to which the spring member is fixed, and a pair of side surface portions that face each other, and the pair of side surface portions preferably sandwich the fixed pulley therebetween and rotatably hold the fixed pulley. According to this structure, when the holding unit is exposed from the support column, a component such as the wire rope held by the holding unit can be exposed from a portion of the holding unit at which the side surface portions are not disposed, and thus the wire rope can be replaced more easily. Furthermore, a support shaft of the fixed pulley can be easily fixed to the holding unit.

In the aforementioned structure in which the holding unit includes the upper surface portion, the bottom surface portion, and the side surface portions, the support column preferably includes a holding unit fixing portion through which a fastener that fixes the holding unit to the support column is attachable from an outside of the support column. According to this structure, the holding unit can be easily fixed to and unfixed from the support column.

In the aforementioned structure in which the support column includes the holding unit fixing portion, the upper surface portion of the holding unit preferably contacts the support column and is preferably supported in the vertical direction by the support column, and the holding unit is preferably fixable to the support column by the fastener in a state in which the holding unit does not move in the vertical direction with respect to the support column. According to this structure, in a state in which the holding unit is stabilized in the vertical direction, the holding unit can be fixed to and unfixed from the support column by the fastener. Consequently, the holding unit can be more easily fixed to and unfixed from the support column.

In the aforementioned structure in which the holding unit includes the upper surface portion, the bottom surface portion, and the side surface portions, an upper end of the spring member is preferably disposed on a lower surface of the bottom surface portion, a lower end of the spring member is preferably held by a spring holding member attached to another end of a shaft, one end of which is fixed to a moving pulley holder that holds the moving pulley, and the spring member is preferably a compression spring that urges the moving pulley substantially vertically downward. According to this structure, in the structure in which the X-ray generator is supported so as to be able to move up and down using the elastic force of the compression spring, the wire rope can be easily replaced.

In the aforementioned structure in which the holding unit includes the upper surface portion, the bottom surface portion, and the side surface portions, an upper end of the spring member is preferably held by a moving pulley holder that holds the moving pulley, a lower end of the spring member is preferably held by a spring holding member that holds a holder, one end of which is held by the bottom surface portion, and the spring member is preferably a tension spring that urges the moving pulley substantially vertically downward. According to this structure, in the structure in which the X-ray generator is supported so as to be able to move up and down using the elastic force of the tension spring, the wire rope can be easily replaced.

In the aforementioned structure in which the holding unit includes the upper surface portion, the bottom surface portion, and the side surface portions, the holding unit preferably further includes a hoist portion provided on an upper surface of the upper surface portion to hoist the holding unit vertically upward. According to this structure, using the hoist portion, the holding unit can be hoisted vertically upward, and thus the holding unit can be more easily exposed from the support column. Consequently, the workability of wire rope replacement in the field can be further improved.

The aforementioned structure in which the holding unit includes the upper surface portion, the bottom surface portion, and the side surface portions preferably further includes an opening for maintenance provided in a side surface of the support column, and an elevating mechanism that raises and lowers the holding unit and is detachable from the support column via the opening. According to this structure, when the holding unit is moved vertically upward with respect to the support column, it is not necessary to use a space above the holding unit, and thus the wire rope can be easily replaced even when the ceiling is low. Consequently, the workability of wire rope replacement in the field can be further improved. Moreover, it is not necessary to attach the elevating mechanism to the support column except when the wire rope is replaced, and thus the weight of the X-ray apparatus for rounds can be reduced by detaching the elevating mechanism.

Effect of the Invention

As described above, according to the present invention, it is possible to provide an X-ray apparatus for rounds in which the workability of wire rope replacement is improved.

MODES FOR CARRYING OUT THE INVENTION

Embodiments embodying the present invention are hereinafter described on the basis of the drawings.

First Embodiment (Structure of X-Ray Apparatus for Rounds)

The overall structure of an X-ray apparatus 1 for rounds according to a first embodiment of the present invention is now described with reference to FIG. 1.

Figure 1:
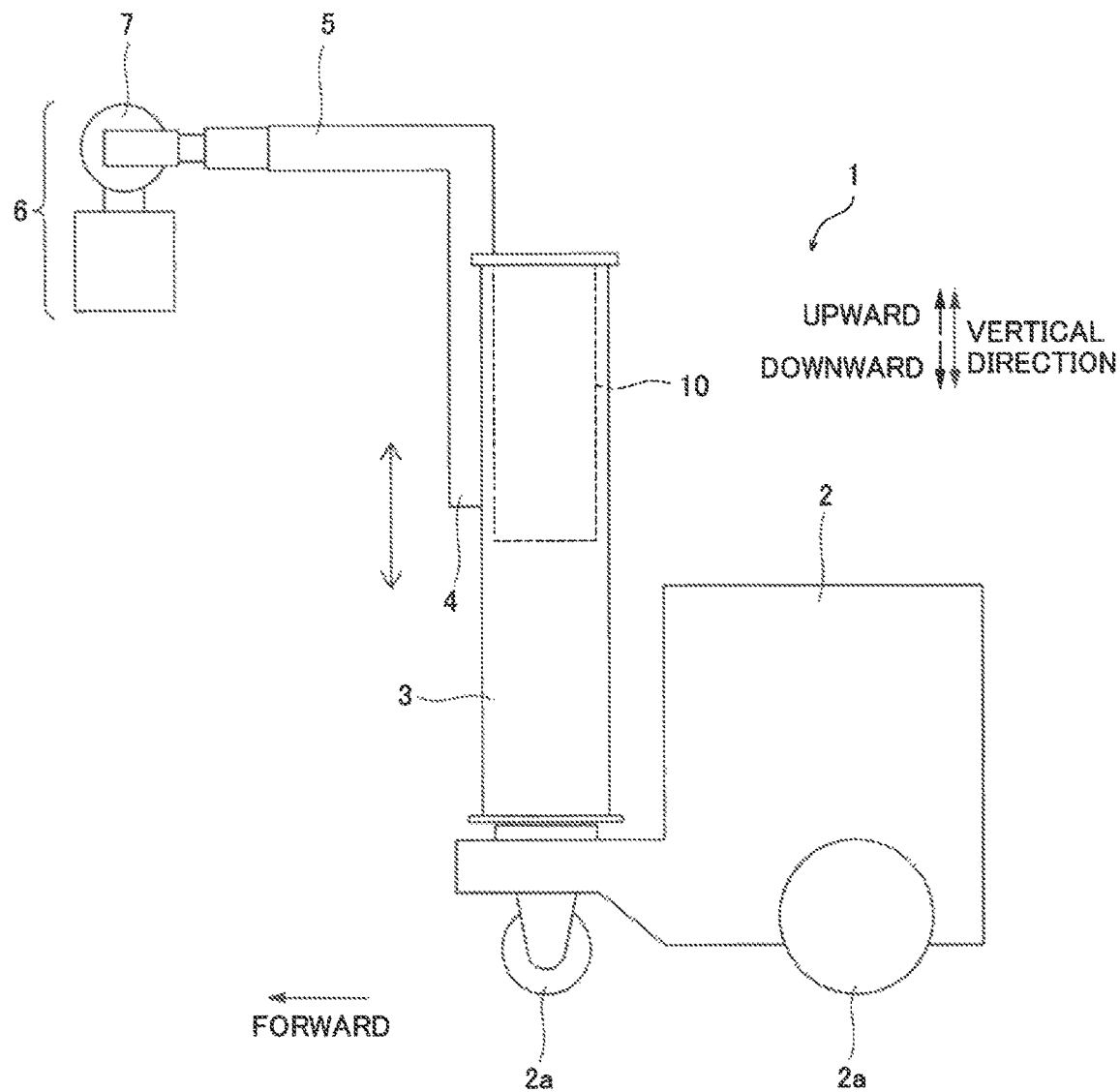
FIG. 1 is a diagram showing the overall structure of an X-ray apparatus for rounds according to a first embodiment of the present invention.

As shown in FIG. 1, the entire X-ray apparatus 1 for rounds according to the first embodiment is movable, and at the time of rounds, the X-ray apparatus 1 for rounds can move to a patient (subject) in each hospital room to perform X-ray imaging. The X-ray apparatus 1 for rounds includes a main body 2, a support column 3, an intermediate portion 4, an arm 5, and an X-ray generator 6.

The main body 2 includes a power supply, a battery, an operation panel, etc. Furthermore, a plurality of wheels 2a are provided at a lower portion of the main body 2, and the X-ray apparatus 1 for rounds can be moved.

The support column 3 is attached to a front portion of the main body 2 so as to extend in a vertical direction. The support column 3 is hollow, and a holding frame 10 that holds a component that can raise and lower the intermediate portion 4 (eventually the X-ray generator 6) is housed inside the support column 3. The holding frame 10 is an example of a "holding unit" in the claims.

The intermediate portion 4 is attached to the front side of the support column 3 so as to be movable in the vertical direction. The arm 5 is provided on an upper portion of the intermediate portion 4 so as to extend forward of the intermediate portion 4.

The X-ray generator 6 is provided at an end of the arm 5 opposite to the intermediate portion 4, and includes an X-ray tube 7 including an X-ray source inside. The height position of the X-ray tube 7 can be changed as the intermediate portion 4 moves up and down.

As described above, the X-ray apparatus 1 for rounds according to the first embodiment moves to a patient (subject) by the plurality of wheels 2a, and X-rays can be emitted from the height position of the X-ray tube 7 adjusted by the component held by the holding frame 10.

(Structure of Support Column and Holding Frame)

The structure of the support column 3 and the holding frame 10 housed inside the support column 3 is now described with reference to FIGS. 2 to 4.

Figure 2:
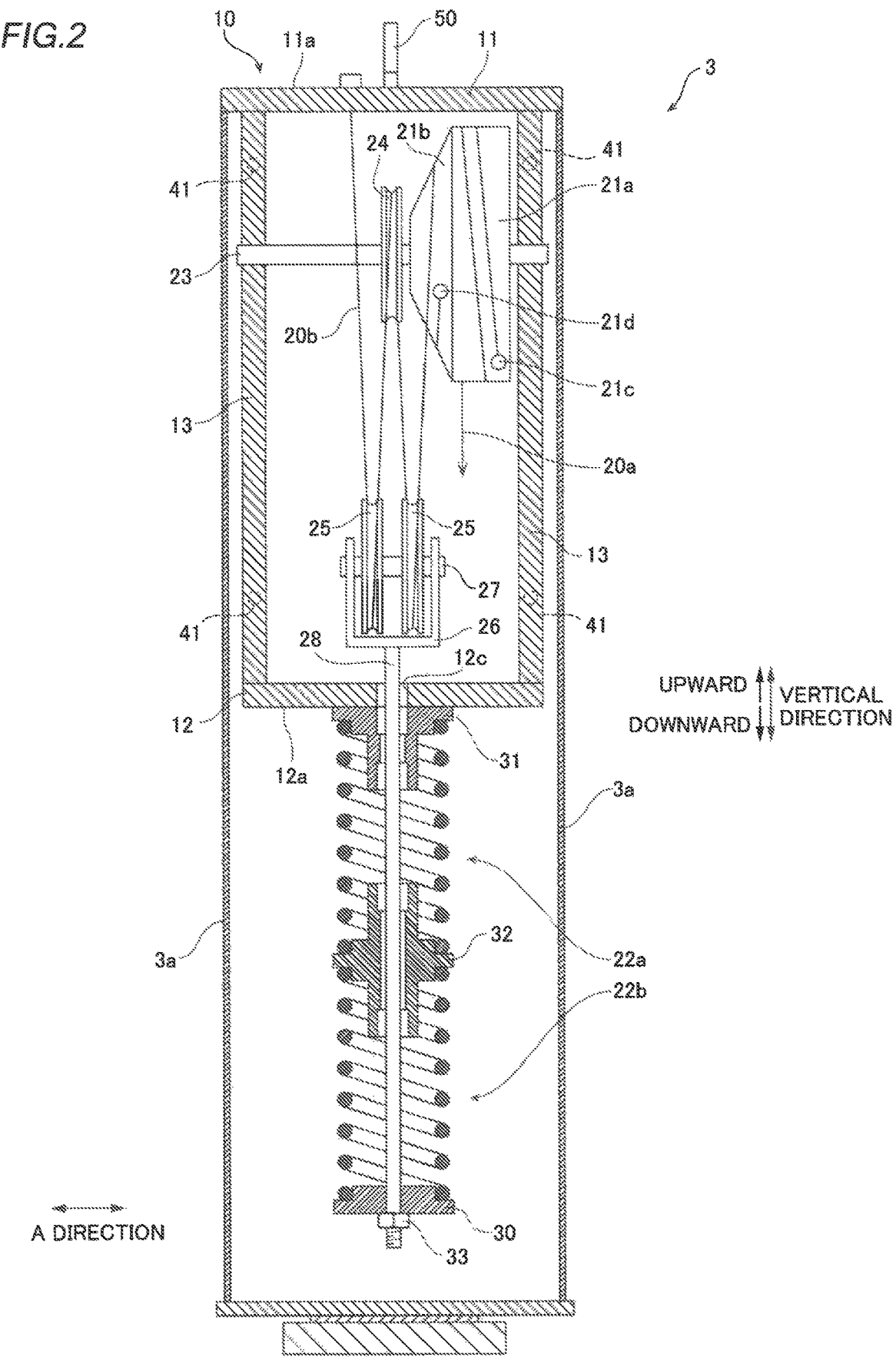
FIG. 2 is a front view illustrating the details of a holding unit according to the first embodiment of the present invention.
Figure 3:
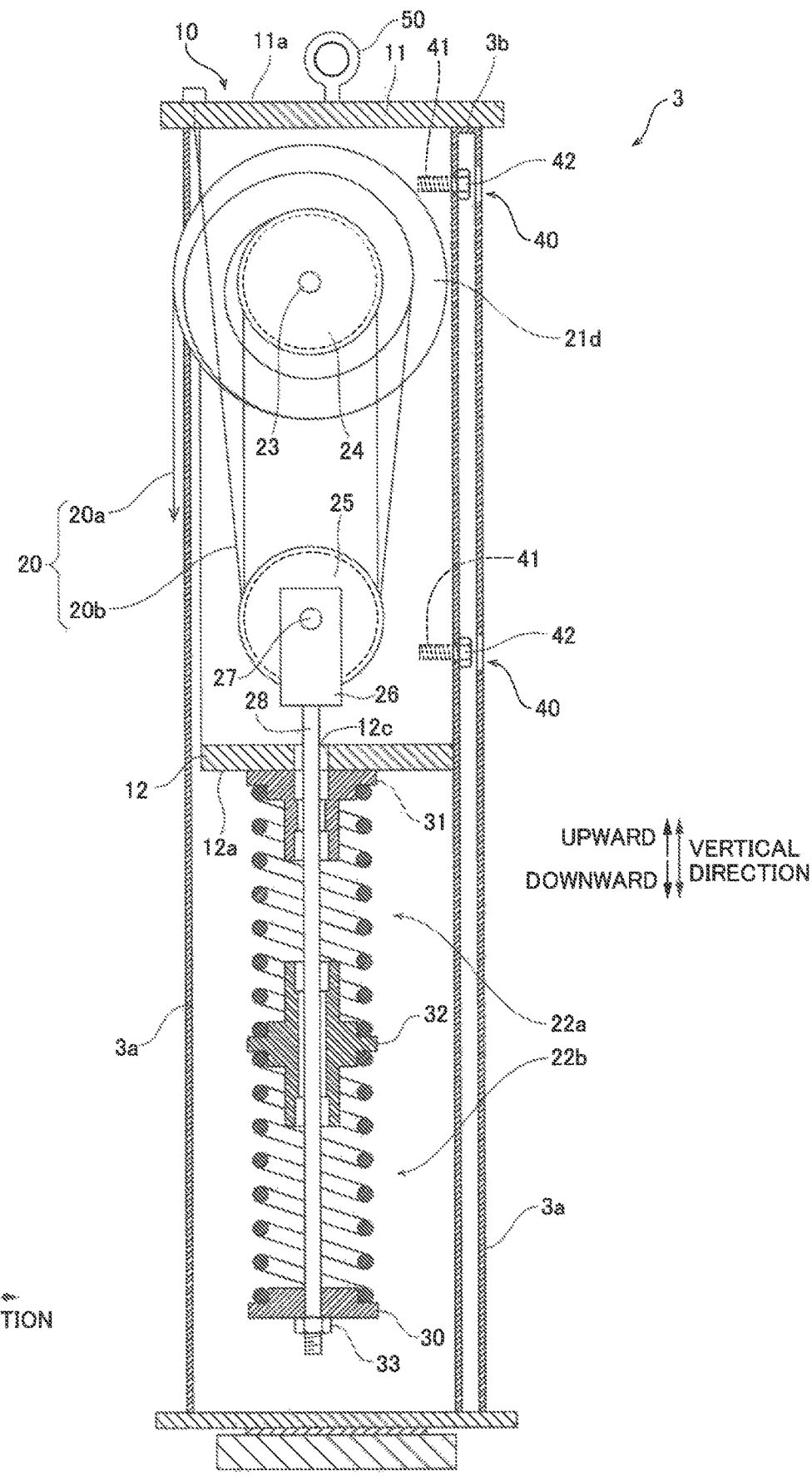
FIG. 3 is a side view illustrating the details of the holding unit according to the first embodiment of the present invention.
Figure 4:
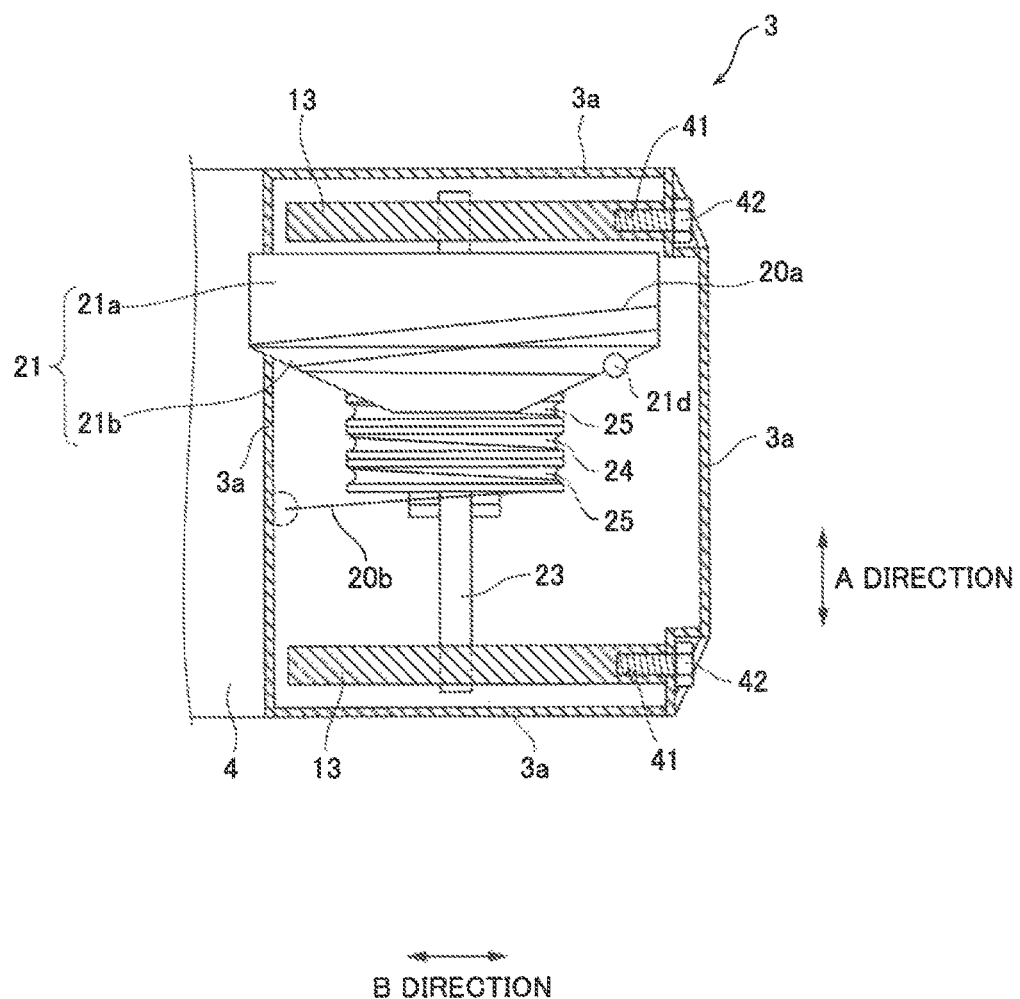
FIG. 4 is a plan view illustrating the details of the holding unit according to the first embodiment of the present invention.

In the support column 3, as shown in FIGS. 2 to 4, the holding frame 10 is housed in an internal portion surrounded by a plurality of plate-shaped side surfaces 3a. An upper portion of the support column 3 is open, and the holding frame 10 can be housed inside the support column 3 from the upper side of the support column 3. The side surfaces 3a include openings 40 into which holding frame fixing screws 42 that fix the holding frame 10 to the support column 3 are inserted. The holding frame fixing screws 42 are attached from the outside of the support column 3 such that the holding frame 10 is fixed to the support column 3. The holding frame fixing screws 42 and the openings 40 are examples of a "fastener" and a "holding unit fixing portion" in the claims, respectively.

The holding frame 10 includes a plate-shaped upper surface holding frame 11 disposed at an upper portion of the holding frame 10, a plate-shaped lower surface holding frame 12 disposed at a lower portion of the holding frame 10, and plate-shaped side surface holding frames 13 disposed between the upper surface holding frame 11 and the lower surface holding frame 12, and the holding frame 10 has a frame shape. The upper surface holding frame 11 and the side surface holding frames 13 are fixed to each other by fixing screws (not shown), and the lower surface holding frame 12 and the side surface holding frames 13 are fixed to each other by fixing screws (not shown). The upper surface holding frame 11, the lower surface holding frame 12, and the side surface holding frames 13 are examples of an "upper surface portion", a "bottom surface portion", and a "side surface portion" in the claims, respectively.

The upper surface holding frame 11 has a size substantially equal to that of the support column 3 or larger than that of the support column 3 so as to cover the entire support column 3 in a plan view. Thus, in a state in which the holding frame 10 is housed in the support column 3, the upper surface holding frame 11 contacts the upper surface 3b of the support column 3, and is supported by the upper surface 3b of the support column 3 in the vertical direction. Thus, in the state in which the holding frame 10 is housed in the support column 3, the upper holding frame 11 can prevent the holding frame 10 from further moving vertically downward. In this state, the holding frame 10 is fixed to the support column 3 by the holding frame fixing screws 42. Furthermore, a hoist ring 50 used to hoist the holding frame 10 vertically upward is provided on the upper surface 11a of the upper surface holding frame 11. Furthermore, one end of a wire rope 20b is fixed to the upper surface holding frame 11. In addition, the hoist ring 50 is an example of a "hoist portion" in the claims.

The lower surface holding frame 12 is smaller than the support column 3 in a plan view. The lower surface holding frame 12 is disposed in the vicinity of the center of the height position of the support column 3 in the state in which the holding frame 10 is housed in the support column 3. Furthermore, a tip spring seat 31 to which one end of a compression spring 22a is fixed is attached to the lower surface 12a of the lower surface holding frame 12. In a central portion of the lower surface holding frame 12, a through-hole 12c is formed. The compression spring 22a is an example of a "spring member" in the claims.

A pair of side surface holding frames 13 are formed in an A direction. Consequently, the side surface holding frames 13 are not provided in a B direction orthogonal to the A direction of the holding frame 10. Furthermore, a support shaft 23, which is a rotation shaft of a pulley 21 around which a wire rope 20a and the wire rope 20b are wound, is fixed to the side surface holding frames 13. Thus, the pair of side surface holding frames 13 sandwich the pulley 21 therebetween, and rotatably hold the pulley 21. The pulley 21 is an example of a "fixed pulley" in the claims.

The side surface holding frames 13 include screw holes 41 at the same height positions as the height positions of the openings 40 in the state in which the holding frame 10 is housed in the support column 3. Thus, in the state in which the holding frame 10 is housed in the support column 3, the holding frame fixing screws 42 are screwed into the screw holes 41 via the openings 40 of the side surfaces 3a such that the holding frame 10 is fixed to the support column 3. At this time, the side surface holding frames 13 are preferably fixed in contact with the side surfaces 3a of the support column 3. Furthermore, the holding frame fixing screws 42 are unfastened via the openings 40 such that the holding frame 10 is detached from the support column 3 so as to be movable in the vertical direction. Consequently, the holding frame 10 can be hoisted vertically upward so as to be exposed from the support column.

The pulley 21 includes a take-up pulley 21a having a constant radius ratio and a helical pulley 21b having a variable radius ratio. The take-up pulley 21a and the helical pulley 21b are integral and unitary with each other, and share the rotation shaft (support shaft 23). The take-up pulley 21a and the helical pulley 21b respectively include fixing portions 21c and 21d that fix the wire rope 20 including the wire rope 20a and the wire rope 20b. Thus, the wire rope 20b is wound around the helical pulley 21b such that the helical pulley 21b is rotated. The take-up pulley 21a and the helical pulley 21b may be provided separately from each other. In this case, the take-up pulley 21a and the helical pulley 21b are fixed to each other by fastening with a screw or the like, and share the rotation shaft (support shaft 23).

Another end of the wire rope 20a, one end of which is fixed to the intermediate portion 4 (see FIG. 1), is fixed to a fixing portion 21c. Another end of the wire rope 20b, one end of which is fixed to the upper surface holding frame 11, is fixed to a fixing portion 21d. A portion of the wire rope 20a fixed to the intermediate portion 4 is not shown in the figures.

The wire rope 20b is wound around a fixed pulley 24 that shares a rotation axis with the pulley 21 and two moving pulleys 25 disposed below the pulley 21 and that share a rotation axis with each other between the helical pulley 21b and the upper surface holding frame 11. The two moving pulleys 25 share a shaft 27 as a rotation shaft. In addition, the two moving pulleys 25 are held by a holder 26 via the shaft 27. The moving pulleys 25 are movable in the vertical direction above the lower surface holding frame 12. Thus, the moving pulleys 25, the pulley 21, and the wire rope 20 are disposed in upper portions of the support column 3 and the holding frame 10 (above the lower surface holding frame 12). The holder 26 is an example of a "moving pulley holder" in the claims.

Compression springs 22a and 22b are disposed in the lower portion of the holding frame 10. An upper end of the compression spring 22a is held by the tip spring seat 31, and a lower end thereof is held by an upper portion of a relay spring seat 32. An upper end of the compression spring 22b is held by a lower portion of the relay spring seat 32, and a lower end thereof is held by an end spring seat 30. Thus, the compression springs 22a and 22b are disposed in series such that the length of each of the compression springs 22a and 22b is reduced as compared with the case in which one compression spring has the same spring length as that of the compression springs 22a and 22b, and thus buckling of the compression springs 22a and 22b is significantly reduced or prevented. The compression spring 22b is an example of a "spring member" in the claims. The end spring seat 30 is an example of a "spring holding member" in the claims.

The tip spring seat 31, the relay spring seat 32, and the end spring seat 30 each include a through-hole through which a shaft 28 passes at each central portion in a horizontal direction. An upper end of the shaft 28 is fixed to the holder 26. A lower end of the shaft 28 is attached to the end spring seat 30 that holds the compression spring 22b. The shaft 28 passes through the through-hole 12c of the lower surface holding frame 12, the through-hole of the tip spring seat 31, an internal portion of the compression spring 22a, the through-hole of the relay spring seat 32, an internal portion of the compression spring 22b, and the through-hole of the end spring seat 30 in this order from the upper side to lower side. The shaft 28 is fixed to the end spring seat 30 by a nut 33. Consequently, the compression springs 22a and 22b urge the shaft 28 substantially vertically downward so as to urge the moving pulleys 25 substantially vertically downward, and expand and contract as the X-ray generator 6 moves up and down.

(Elevating Mechanism of X-Ray Generator)

An elevating mechanism of the X-ray generator 6 is now described. The X-ray generator 6 moves up and down as the intermediate unit 4 moves up and down, and thus in the following description, it is assumed that the X-ray generator 6 also moves up and down as much as the intermediate portion 4 moves up and down.

When it is attempted to move the intermediate portion 4 vertically downward, the wire rope 20a, one end of which is fixed to the intermediate portion 4, is pulled vertically downward. When the take-up pulley 21a around which the wire rope 20a is wound rotates, the wire rope 20b wound around the helical pulley 21b that rotates coaxially with the take-up pulley 21a is further taken up, and it is attempted to move the moving pulleys 25, around which the wire rope 20b is wound and which make a relay, vertically upward. When the moving pulleys 25 move vertically upward, it is attempted to move the shaft 28, one end of which is fixed to the holder 26 that holds the moving pulleys 25, vertically upward. Then, the end spring seat 30 to which the lower end of the shaft 28 is fixed is pushed vertically upward. That is, a compression force acts on the compression springs 22a and 22b, and thus a substantially vertically downward reaction force (elastic force) is generated on the compression springs 22a and 22b. Then, a portion of the elastic force of the compression springs 22a and 22b is transmitted to the helical pulley 21b via the wire rope 20b, and is canceled through the helical pulley 21b. Thus, the intermediate portion 4 stops at a fixed height position. At this time, the large force of the compression springs 22a and 22b is applied to the wire ropes 20a and 20b, and thus the wire ropes 20a and 20b are easily worn away.

When it is attempted to move the intermediate portion 4 vertically upward, the wire rope 20a, one end of which is fixed to the intermediate portion 4, is pulled vertically upward. Then, the take-up pulley 21a around which the wire rope 20a is wound rotates in an opposite direction to the case in which it is attempted to move the intermediate portion 4 vertically downward such that the wire rope 20b wound around the helical pulley 21b that rotates coaxially with the take-up pulley 21a is drawn out, and it is attempted to move the moving pulleys 25, around which the wire rope 20b is wound and which make a relay, substantially vertically downward. When the moving pulleys 25 move substantially vertically downward, it is attempted to move the shaft 28, one end of which is fixed to the holder 26 that holds the moving pulleys 25, substantially vertically downward. Then, the end spring seat 30 to which the lower end of the shaft 28 is fixed is pushed substantially vertically downward. That is, a force that acts on the compression springs 22a and 22b is reduced. Along with this, a portion of the reduced reaction force (elastic force) is canceled through the helical pulley 21b. Thus, the intermediate portion 4 stops at a fixed height position.

As described above, the elastic force that acts on the compression springs 22a and 22b is not constant due to the expansion and contraction of the springs. Therefore, in the present embodiment, the helical pulley 21b having a variable radius ratio is set as the pulley around which the wire rope 20b is wound such that the length of the wire rope 20b to be taken up is changed.

(Method for Moving Holding Frame in Vertical Direction with Respect to Support Column)

A method for moving the holding frame 10 in the vertical direction with respect to the support column 3 is now described with reference to FIGS. 5 and 6.

Figure 5:
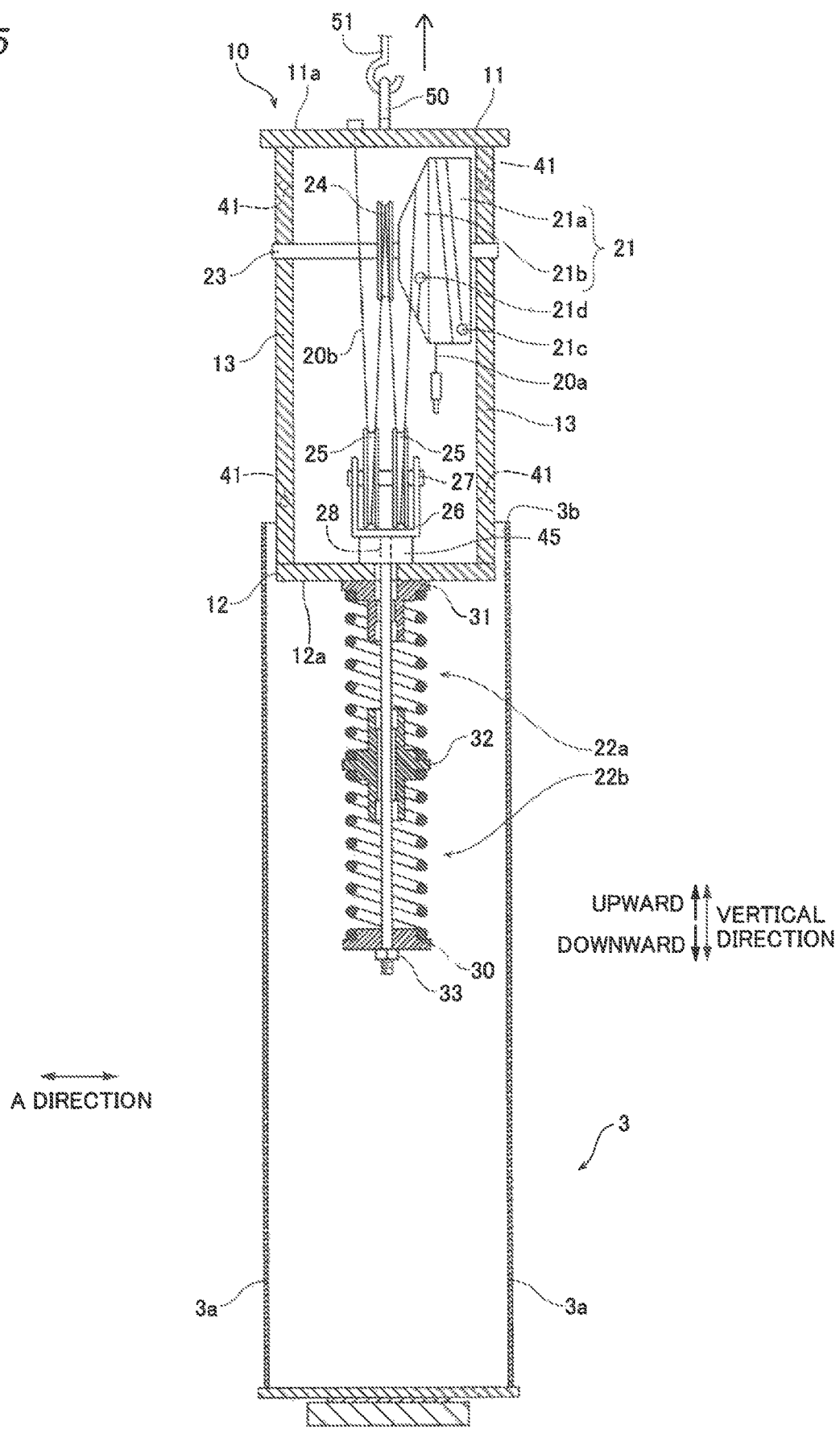
FIG. 5 is a front view illustrating a state in which the holding unit according to the first embodiment of the present invention is exposed from a support column.
Figure 6:
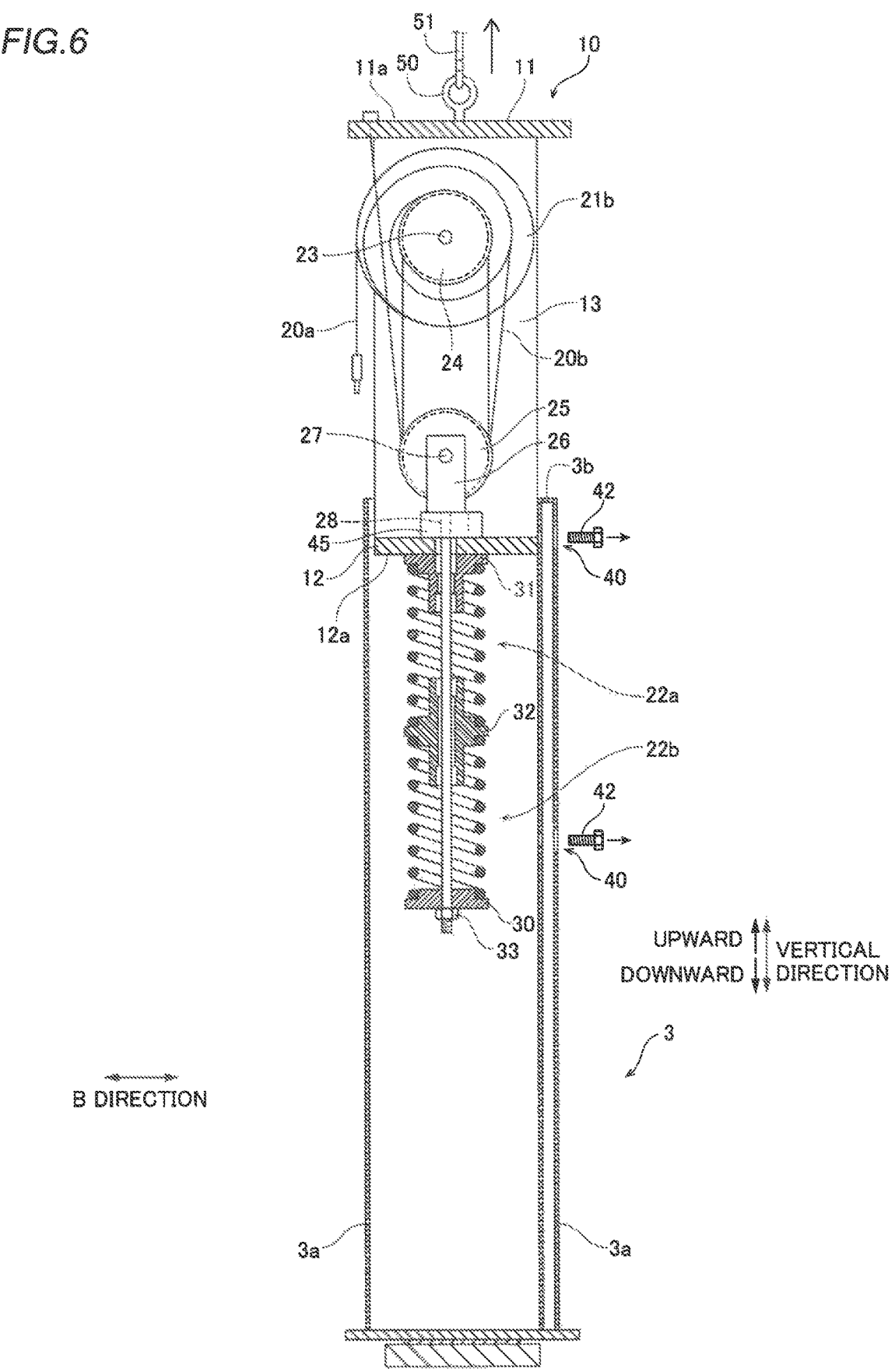
FIG. 6 is a side view illustrating the state in which the holding unit according to the first embodiment of the present invention is exposed from the support column.

First, as shown in FIGS. 5 and 6, a hoist 51 having a hook-shaped tip is attached to the hoist ring 50. Next, as shown in FIG. 6, the holding frame fixing screws 42 are removed from the openings 40 and the screw holes 41.

Then, an insertion wood 45 is inserted between the holder 26 and the lower surface holding frame 12 in order not to bring the holder 26 close to the lower surface holding frame 12 by a predetermined distance or longer. The insertion wood 45 restricts movement of the shaft 28 with respect to the holder 26 and the lower surface holding frame 12, and thus the urging force of the compression springs 22a and 22b is nullified.

Next, after the intermediate portion 4 is fixed by a method such as pinning, fixing of one end of the wire rope 20a fixed to the intermediate portion 4 is released. Thus, the holding frame 10, and the pulley 21, the compression springs 22a and 22b, and the wire ropes 20a and 20b held by the holding frame 10 can be moved with respect to the support column 3. Then, the holding frame 10 is hoisted (moved upward) by the hoist 51 such that the holding frame 10 can be moved upward of the support column 3.

Replacement of the wire ropes 20a and 20b is performed in a state in which the pulley 21, the fixed pulley 24, and the moving pulleys 25, around which the wire ropes 20a and 20b are wound, together with the holding frame 10 are exposed upward of the support column 3. Therefore, the wire ropes 20a and 20b can be replaced by moving the holding frame 10 vertically upward to a height at which the pulley 21 and the moving pulleys 25 provided in the upper portion of the holding frame 10 are exposed.

Effects of First Embodiment

According to the first embodiment, the following effects are achieved.

According to the first embodiment, as described above, the holding frame 10 that holds the wire rope 20 is housed in the support column 3 that extends in the vertical direction such that the holding frame 10 can be detached and upwardly exposed. Accordingly, the holding frame 10 that holds the wire rope 20 is moved upward of the support column 3 such that the holding frame 10 can be easily exposed from the support column 3. Therefore, the wire rope 20 held by the holding frame 10 can be replaced without disassembling the support column 3, and thus the workability of wire rope replacement can be improved. Moreover, even in the field, wire rope replacement can be performed, and thus it is possible to prevent prolongation of a period during which the X-ray apparatus 1 for rounds cannot be used due to taking the wire rope back to the factory for wire rope replacement.

According to the first embodiment, as described above, the wire rope 20 is held in the upper portion of the holding frame 10, and the holding frame 10 is detached from the support column 3 and moved upward of the support column 3 so as to be exposed from the support column 3. Accordingly, the wire rope 20 can be replaced by moving the holding frame 10 upward until the upper portion of the holding frame 10 is exposed from the support column 3, and thus as compared with the case in which the holding frame 10 is moved upward until the entire holding frame 10 is exposed from the support column 3, the height to which the holding frame 10 is moved upward can be reduced, and the wire rope 20 can be replaced even when the ceiling is low. Consequently, the wire rope 20 can be replaced more easily.

According to the first embodiment, as described above, the holding frame 10 further holds the moving pulleys 25 around which the wire rope 20 is wound and which move up and down as the compression springs 22a and 22b expand and contract, the wire rope 20, the pulley 21, and the moving pulleys 25 are held in the upper portion of the holding frame 10, and the compression springs 22a and 22b are held in the lower portion of the holding frame 10. Accordingly, the wire rope 20 can be easily removed from the moving pulleys 25 and the pulley 21 by moving the holding frame 10 upward until the upper portion of the holding frame 10 is exposed from the support column 3. Consequently, the wire rope 20 can be replaced more easily.

According to the first embodiment, as described above, the holding frame 10 has a frame shape including the upper surface holding frame 11 to which the wire rope 20 is fixed, the lower surface holding frame 12 to which the compression springs 22a and 22b are fixed, and the pair of side surface holding frames 13 that face each other, and the pair of side surface holding frames 13 sandwich the pulley 21 therebetween and rotatably hold the pulley 21. Accordingly, when the holding frame 10 is exposed from the support column 3, a component such as the wire rope 20 held by the holding frame 10 can be exposed from a portion of the holding frame 10 at which the side holding frames 13 are not disposed, and thus the wire rope 20 can be replaced more easily. Furthermore, the support shaft 23 of the pulley 21 can be easily fixed to the holding frame 10.

According to the first embodiment, as described above, the support column 3 includes the openings 40 through which the holding frame fixing screws 42 that fix the holding frame 10 to the support column 3 are attachable from the outside of the support column 3. Accordingly, the holding frame 10 can be easily fixed to and unfixed from the support column 3.

According to the first embodiment, as described above, the upper surface holding frame 11 of the holding frame 10 contacts the support column 3 and is supported in the vertical direction by the support column 3, and the holding frame 10 can be fixed to the support column 3 by the holding frame fixing screws 42 in a state in which the holding frame 10 does not move in the vertical direction with respect to the support column 3. Accordingly, in a state in which the holding frame 10 is stabilized in the vertical direction, the holding frame 10 can be fixed to and unfixed from the support column 3 by the holding frame fixing screws 42. Consequently, the holding frame 10 can be more easily fixed to and unfixed from the support column 3.

According to the first embodiment, as described above, the upper end of the compression spring 22a is disposed on the lower surface 12a of the lower surface holding frame 12, the lower end of the compression spring 22b is held by the end spring seat 30 attached to another end of the shaft 28, one end of which is fixed to the holder 26 that holds the moving pulleys 25, and the compression springs 22a and 22b are compression springs that urge the moving pulleys 25 substantially vertically downward. Accordingly, in the structure in which the X-ray generator 6 is supported so as to be able to move up and down using the elastic force of the compression springs 22a and 22b, the wire rope 20 can be easily replaced.

According to the first embodiment, as described above, the holding frame 10 further includes the hoist ring 50 provided on the upper surface 11a of the upper surface holding frame 11 to hoist the holding frame 10 vertically upward. Accordingly, using the hoist ring 50, the holding frame 10 can be hoisted vertically upward, and thus the holding frame 10 can be more easily exposed from the support column 3. Consequently, the workability of wire rope replacement in the field can be further improved.

Second Embodiment

A second embodiment is now described with reference to FIGS. 7 and 8. In this second embodiment, an example in which a tension spring is used unlike the structure according to the aforementioned first embodiment in which the compression springs are used is described. In the second embodiment, the same structures as those of the aforementioned first embodiment are denoted by the same reference numerals, and description thereof is omitted.
(Structure of Support Column and Holding Frame)

Figure 7:
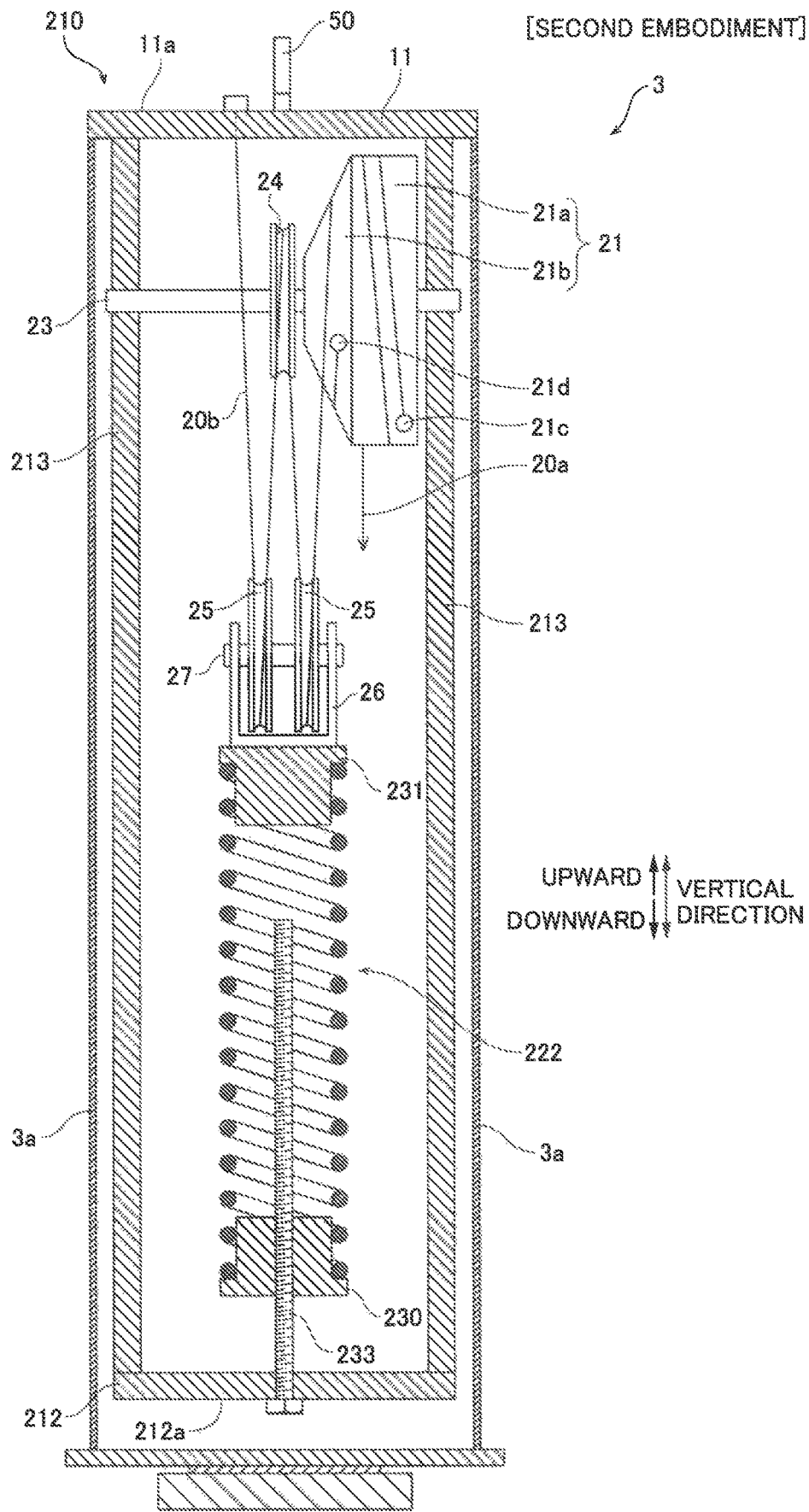
FIG. 7 is a front view illustrating the details of a holding unit according to a second embodiment of the present invention.

As shown in FIG. 7, in the second embodiment of the present invention, a holding frame 210 includes a plate-shaped lower surface holding frame 212 disposed in a lower portion of the holding frame 210, and plate-shaped side surface holding frames 213 disposed between an upper surface holding frame 11 and the lower surface holding frame 12. The lower surface holding frame 212 and the side surface holding frames 213 are examples of a "bottom surface portion" and a "side surface portion" in the claims, respectively.

The lower surface holding frame 212 is disposed in the vicinity of a lower end at the height of a support column 3 in a state in which the holding frame 210 is housed in the support column 3. Furthermore, a spring tension bolt 233 that fixes a tip spring seat 230 to which one end of a tension spring 222 is fixed is attached to the lower surface 212a of the lower surface holding frame 212. The tension spring 222 is an example of a "spring holding member" in the claims. The spring tension bolt 233 is an example of a "holder" in the claims.

A pair of side surface holding frames 213 are provided in an A direction, similarly to the holding frame 10 according to the first embodiment. Consequently, the side surface holding frames 13 are not provided in a B direction orthogonal to the A direction of the holding frame 210. Furthermore, as compared with the holding frame 10 according to the first embodiment, the lengths of the side surface holding frames 213 in a vertical direction with respect to the support column 3 are larger.

The tension spring 222 is disposed in the lower portion of the holding frame 210. An upper end of the tension spring 222 is held by an end spring seat 231, and a lower end thereof is held by the tip spring seat 230.
(Elevating Mechanism of X-Ray Generator)

An elevating mechanism of an X-ray generator 6 is now described.

When it is attempted to move an intermediate portion 4 vertically downward, it is attempted to move moving pulleys 25 vertically upward. When the moving pulleys 25 move vertically upward, a force that pulls the end spring seat 231 vertically upward acts on the end spring seat 231. That is, a force that stretches the tension spring 222 vertically upward acts on the tension spring 222. Thus, a reaction force (elastic force) that acts substantially vertically downward is generated in the tension spring 222. Then, a portion of the elastic force of the tension spring 222 is transmitted to a helical pulley 21b via a wire rope 20b, and is canceled through the helical pulley 21b. Thus, the intermediate portion 4 stops at a fixed height position.

When it is attempted to move the intermediate portion 4 vertically upward, it is attempted to move the moving pulleys 25 substantially vertically downward. When the moving pulleys 25 move substantially vertically downward, it is attempted to move the end spring seat 231 substantially vertically downward. Thus, a force that acts on the tension spring 222 is reduced. Along with this, a portion of the reduced reaction force (elastic force) is canceled through the helical pulley 21b. Thus, the intermediate portion 4 stops at a fixed height position.
(Method for Moving Holding Frame in Vertical Direction with Respect to Support Column)

A method for moving the holding frame 210 in the vertical direction with respect to the support column 3 is now described with reference to FIG. 8.

Figure 8:
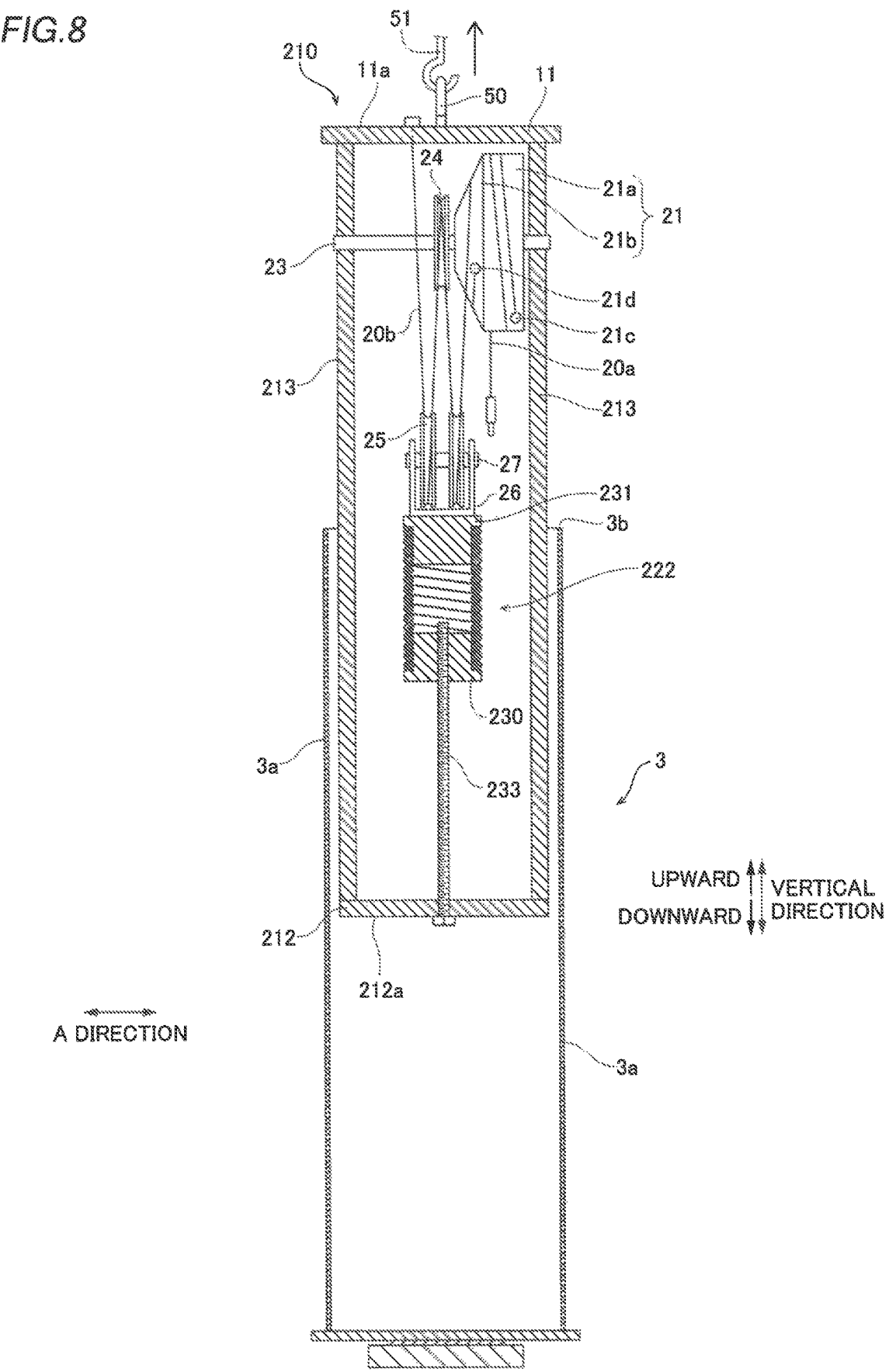
FIG. 8 is a front view illustrating a state in which the holding unit according to the second embodiment of the present invention is exposed from a support column.

First, as shown in FIG. 8, a hoist 51 having a hook-shaped tip is attached to a hoist ring 50. Next, similarly to the first embodiment, holding frame fixing screws 42 are removed from openings 40 and screw holes 41.

Then, the spring tension bolt 233 that fixes the tip spring seat 230 to the lower surface holding frame 212 is loosened with a tool such as a wrench through an opening (not shown) provided in a lower portion of the side surface 3a of the support column 3. Thus, a force that pulls the tension spring 222 no longer acts on the tension spring 222, and thus the urging force of the tension spring 222 that acts substantially vertically downward is nullified. Then, the holding frame 210 is moved vertically upward to a height at which a pulley 21 and the moving pulleys 25 provided in an upper portion of the holding frame 210 are exposed such that wire ropes 20a and 20b can be replaced.

The remaining structures of the second embodiment are similar to those of the aforementioned first embodiment.

Effects of Second Embodiment

According to the second embodiment, the following effects are achieved.

According to the second embodiment, as described above, the upper end of the tension spring 222 is held by a holder 26 that holds the moving pulleys 25, the lower end of the tension spring 222 is held by the tip spring seat 230 that holds the spring tension bolt 233, one end of which is held by the lower surface holding frame 212, and the tension spring 222 is a tension spring that urges the moving pulleys 25 substantially vertically downward. Accordingly, in the structure in which the X-ray generator 6 is supported so as to be able to move up and down using the elastic force of the tension spring 222, the wire rope 20 can be easily replaced.

The remaining effects of the second embodiment are similar to those of the aforementioned first embodiment.

Modified Example of Second Embodiment

A modified example of the second embodiment is now described with reference to FIGS. 9 and 10. In this modified example of the second embodiment, an example in which a holding frame 10 is moved vertically upward from a support column 3 by a method different from that according to the aforementioned second embodiment is described. In the modified example of the second embodiment, the same structures as those of the aforementioned second embodiment are denoted by the same reference numerals, and description thereof is omitted.

Figure 9:
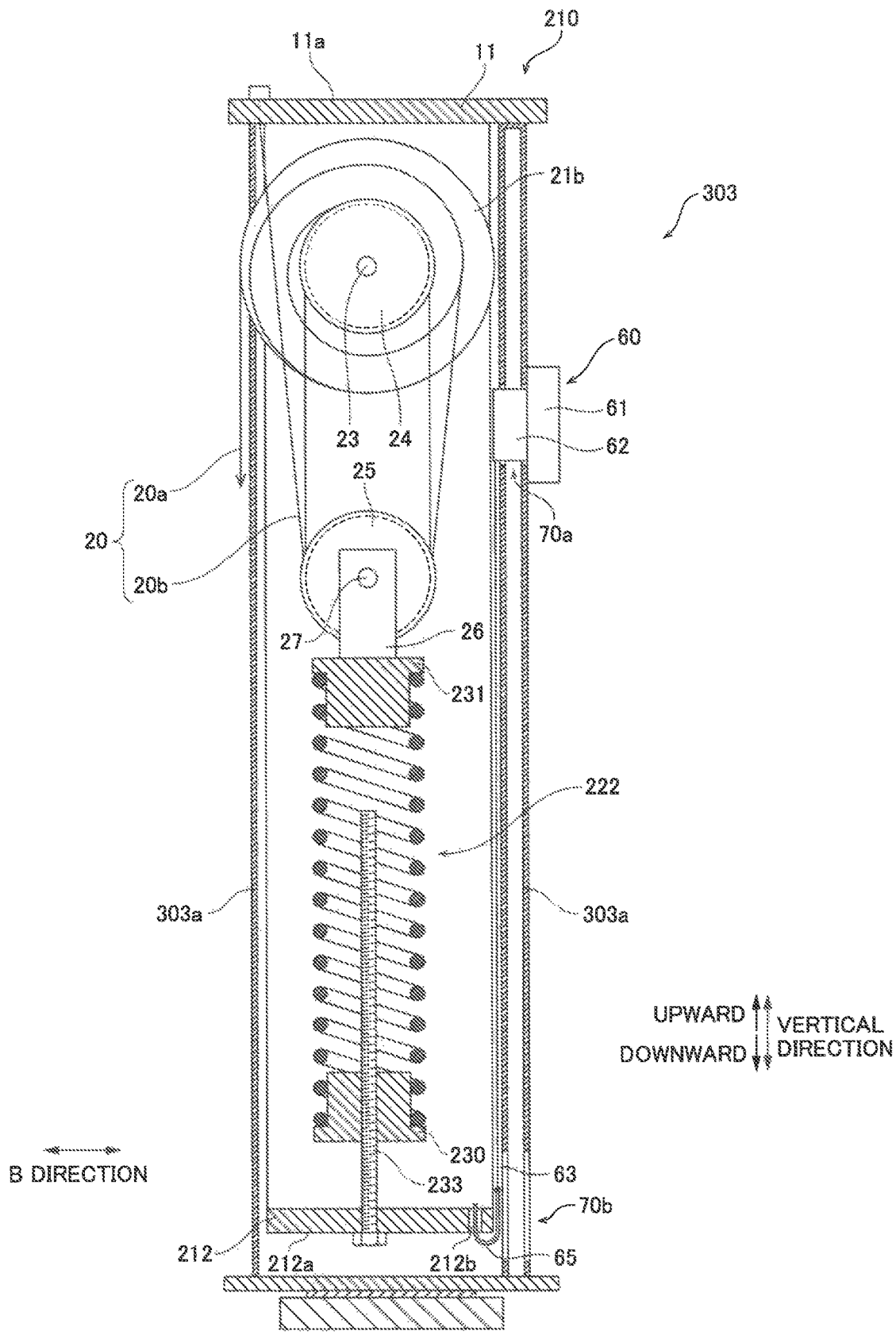
FIG. 9 is a side view illustrating the details of a holding unit according to a modified example of the second embodiment of the present invention.
Figure 10:
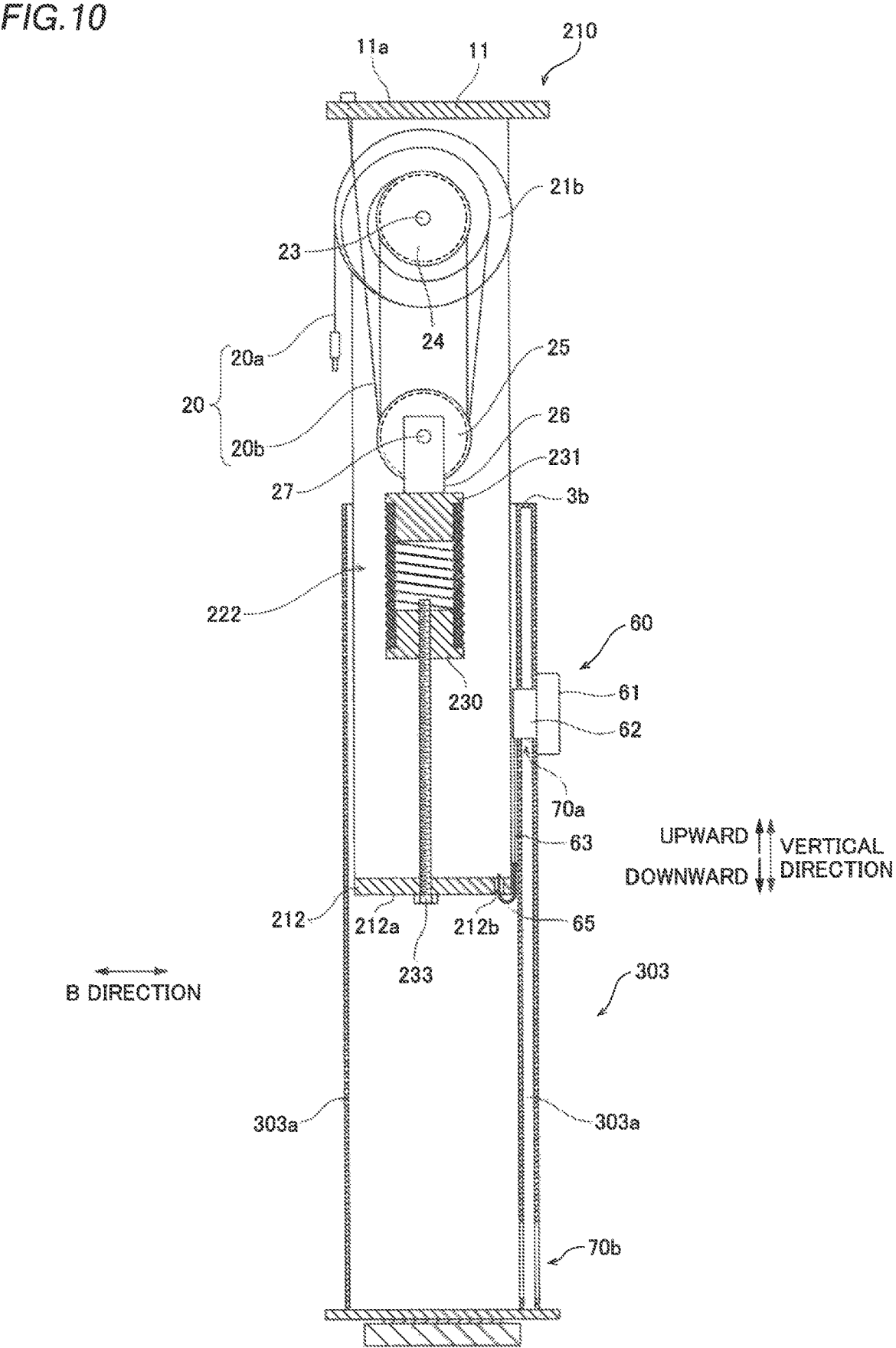
FIG. 10 is a side view illustrating a state in which the holding unit according to the modified example of the second embodiment of the present invention is exposed from a support column.

As shown in FIG. 9, in the modified example of the second embodiment of the present invention, openings 70a and 70b for maintenance are provided in a side surface 303a of a support column 303. A lifting device 60 that moves a holding frame 210 vertically upward in order to expose the holding frame 210 from the support column 3 can be attached to the opening 70a. The lifting device 60 is an example of an "elevating mechanism" in the claims.

The lifting device 60 includes a main body 61 exposed outward of the side surface 303a of the support column 303 through the opening 70a, a winder 62 including a drum disposed inside the opening 70a and that winds a wire rope 63, the wire rope 3, and a hook 65 attached to the tip of the wire rope 63. A handle (not shown) is attached to the main body 61, and the handle is operated such that the winder 62 can wind the wire rope 63. Furthermore, the tip of the hook 65 is inserted into a hole 212b provided in a lower surface holding frame 212 and is hooked into the lower surface holding frame 212 such that the hook 65 can be fixed to the lower surface holding frame 212. The opening 70b is provided for a user to access the hole 212b when the tip of the hook 65 is inserted or removed. Thus, as shown in FIG. 10, the holding frame 210 fixed by the hooks 65 can be moved vertically upward according to the winding amount of the wire rope 63 accompanying the operation of the handle. In addition, the lifting device 60 is detachable from the support column 303 via the opening 70a provided in the side surface 303a of the support column 303, and is lightweight and portable. Therefore, the holding frame 210 can be easily moved up and down by bringing the lifting device 60 into the field and attaching the lifting device 60 to the support column 303 when replacing a wire rope 20. In addition, the lifting device 60 is detached except when the wire rope 20 is replaced such that an increase in the weight of an X-ray apparatus 1 for rounds can be significantly reduced or prevented.

The remaining structures of the modified example of the second embodiment are similar to those of the aforementioned first embodiment.

Effects of Modified Example of Second Embodiment

According to the modified example of the second embodiment, the following effects are achieved.

According to the modified example of the second embodiment, as described above, the opening 70a for maintenance is provided in the side surface 303a of the support column 303, and the lifting device 60 that raises and lowers the holding frame 310 is detachable from the support column 303 via the opening 70. Accordingly, when the holding frame 310 is moved vertically upward with respect to the support column 303, it is not necessary to use a space above the holding frame 310, and thus the wire rope 20 can be easily replaced even when the ceiling is low. Consequently, the workability of wire rope replacement in the field can be further improved. Moreover, it is not necessary to attach the lifting device 60 to the support column 303 except when the wire rope 20 is replaced, and thus the weight of the X-ray apparatus 1 for rounds can be reduced by detaching the lifting device 60.

The remaining effects of the modified example of the second embodiment are similar to those of the aforementioned second embodiment.

MODIFIED EXAMPLES

The embodiments and the modified example disclosed this time must be considered as illustrative in all points and not restrictive. The scope of the present invention is not shown by the above description of the embodiment but by the scope of claims for patent, and all modifications (modified examples) within the meaning and scope equivalent to the scope of claims for patent are further included.

In the aforementioned modified example of the second embodiment, the holding frame 210 is lifted with the lifting device 60 unlike the aforementioned second embodiment in which the holding frame 210 is hoisted using the hoist ring 50. Similarly to this, in the aforementioned first embodiment, the holding frame 10 may be lifted with a lifting device.

While the pair of side surface holding frames 13 of the holding frame 10 and the pair of side surface holding frames 213 of the holding frame 210 are provided, and the holding frames 10 and 210 include portions in which the side surface holding frames are not provided in the aforementioned first and second embodiments, the present invention is not restricted to this. According to the present invention, four side surface holding frames may be respectively provided on all four sides, or four or more side surface holding frames may be provided. In this case, in order to improve the workability of wire rope replacement, it is preferable to provide an opening in any of the side surface holding frames.

While the hoist ring 50 and the lifting device 60 are used to move the holding frames 10 and 210 in the vertical direction in the aforementioned first and second embodiments, the present invention is not restricted to this. According to the present invention, the holding frames 10 and 210 can be replaced by other mechanisms capable of moving in the vertical direction.

While the hoist ring 50 used to hoist the holding frame 10 vertically upward is provided on the upper surface 11a of the upper surface holding frame 11 in the aforementioned first and second embodiments, the present invention is not restricted to this. According to the present invention, as the lifting device 60 according to the aforementioned modified example of the second embodiment, the hoist ring 50 may be detachable from the upper surface holding frame 11, and may be lightweight and portable.

While the tip of the hook 65 is inserted into the hole 212b provided in the lower surface holding frame 212 and is hooked into the lower surface holding frame 212 such that the hook 65 is fixable to the lower surface holding frame 212 in the aforementioned modified example of the second embodiment, the present invention is not restricted to this. According to the present invention, a component other than the hook 65 may be used as long as the same is fixable to the lower surface holding frame 212.

While the intermediate portion 4, the arm 5, and the X-ray generator 6 are fixed, and when the intermediate portion 4 moves up and down, the height positions of the intermediate portion 4, the arm 5, and the X-ray generator 6 change by the same amount in the aforementioned first and second embodiments, the present invention is not restricted to this. According to the present invention, in addition to the elevating mechanism between the support column 3 and the intermediate portion 4, another elevating mechanism may be provided between the intermediate portion 4 and the arm 5.

While the upper surface holding frame 11 is substantially equal in size to the support columns 3 and 303 or larger in size than the support columns 3 and 303 so as to cover the entire support columns 3 and 303 in a plan view in the aforementioned first and second embodiments, the present invention is not restricted to this. According to the present invention, as long as the upper surface holding frame 11 can prevent the holding frames 10 and 210 from further moving vertically downward in a state in which the holding frames 10 and 210 are housed in the support columns 3 and 303, the upper surface holding frame 11 may be smaller in size than the support columns 3 and 303 in a plan view. In this case, for example, protrusions that support the upper surface holding frame 11 may be provided inside the side surfaces 3a and 303a of the support columns 3 and 303, or the upper ends of the support columns 3 and 303 may be bent inward of the support columns 3 and 303, and the upper surface holding frame 11 may be supported by the bent portion.

While the wire rope 20a wound around the take-up pulley 21a and the wire rope 20b wound around the helical pulley 21b are separate from each other in the aforementioned first and second embodiments, the present invention is not restricted to this. According to the present invention, the fixing portion 21c to which one end of the wire rope 20a is fixed and the fixing portion 21d to which one end of the wire rope 20b is fixed may not be provided, and one wire rope may be used.

While the tip spring seat 31 is disposed on the lower surface 12a of the lower surface holding frame 12 in the aforementioned first embodiment, the present invention is not restricted to this. According to the present invention, the lower surface holding frame 12 and the tip spring seat 31 may be integral and unitary with each other.

While as a spring mechanism, the two compression springs 22a and 22b are connected in series to each other in the aforementioned first embodiment, the present invention is not restricted to this. According to the present invention, the spring mechanism may include one compression spring. Alternatively, the spring mechanism may include three or more compression springs connected in series to each other.

While the wire rope 20b relays one fixed pulley 24 and the two moving pulleys 25 in the aforementioned first and second embodiments, the present invention is not restricted to this. According to the present invention, the wire rope 20b may relay only one moving pulley 25. Alternatively, the wire rope 20b may relay two fixed pulleys 24 and three moving pulleys 25.

While one wire rope 20a and one wire rope 20b are provided in the aforementioned first and second embodiments, the present invention is not restricted to this. According to the present invention, two wire ropes 20a and two wire ropes 20b may be provided, or three or more wire ropes 20a and three or more wire ropes 20b may be provided. The wire ropes are multiplexed in this manner such that falling of the intermediate portion 4 (eventually the X-ray generator 6) can be significantly reduced or prevented even when one of the wire ropes 20a and 20b is disconnected.

DESCRIPTION OF REFERENCE NUMERALS

1: X-ray apparatus for rounds
3, 303: support column
3a, 303a: side surface (of the support column)
3b: upper surface (of the support column)
6: X-ray generator 10, 210: holding frame (holding unit)
11: upper surface holding frame (upper surface portion)
11a: upper surface (of the upper surface portion)
12, 212: lower surface holding frame (bottom surface portion)
12a, 212a: lower surface (of the bottom surface portion)
13, 213: side surface holding frame (side surface portion)
20 (20a, 20b): wire rope
21: pulley (fixed pulley)
22a, 22b: compression spring (spring member)
25: moving pulley
26: holder (moving pulley holder)
28: shaft
30: end spring seat (spring holding member)
40: opening (holding unit fixing portion)
42: holding frame fixing screw (fastener)
50: hoist ring (hoist portion)
60: lifting device (elevating mechanism)
70a: opening
222: tension spring (spring member)
230: tip spring seat (spring holding member)
233: spring tension bolt (holder)

The invention claimed is:

1. An X-ray apparatus for rounds comprising:
an X-ray generator including an X-ray source that irradiates a subject with X-rays, and capable of moving up and down in a vertical direction;
a holding unit that holds a spring member that expands and contracts as the X-ray generator moves up and down such that the spring member is expandable and contractable, that holds a wire rope that transmits an elastic force of the spring member to the X-ray generator and a fixed pulley around which the wire rope is wound and which rotates, and that supports the X-ray generator such that the X-ray generator is movable up and down; and
a support column that extends in the vertical direction and houses the holding unit such that the holding unit is detachable and upwardly exposable.

2. The X-ray apparatus for rounds according to claim 1, wherein
the wire rope is held in an upper portion of the holding unit; and
the holding unit is detached from the support column and moved upward of the support column so as to be exposed from the support column.

3. The X-ray apparatus for rounds according to claim 1, wherein
the holding unit further holds a moving pulley around which the wire rope is wound and which moves up and down as the spring member expands and contracts; and
the wire rope, the fixed pulley, and the moving pulley are held in an upper portion of the holding unit, and the spring member is held in a lower portion of the holding unit.

4. The X-ray apparatus for rounds according to claim 3, wherein
the holding unit has a frame shape including an upper surface portion to which the wire rope is fixed, a bottom surface portion to which the spring member is fixed, and a pair of side surface portions that face each other; and
the pair of side surface portions sandwich the fixed pulley therebetween and rotatably hold the fixed pulley.

5. The X-ray apparatus for rounds according to claim 4, wherein the support column includes a holding unit fixing portion through which a fastener that fixes the holding unit to the support column is attachable from an outside of the support column.

6. The X-ray apparatus for rounds according to claim 5, wherein
   the upper surface portion of the holding unit contacts the support column and is supported in the vertical direction by the support column; and
   the holding unit is fixable to the support column by the fastener in a state in which the holding unit does not move in the vertical direction with respect to the support column.

7. The X-ray apparatus for rounds according to claim 4, wherein
   an upper end of the spring member is disposed on a lower surface of the bottom surface portion;
   a lower end of the spring member is held by a spring holding member attached to another end of a shaft, one end of which is fixed to a moving pulley holder that holds the moving pulley; and
   the spring member is a compression spring that urges the moving pulley substantially vertically downward.

8. The X-ray apparatus for rounds according to claim 4, wherein
   an upper end of the spring member is held by a moving pulley holder that holds the moving pulley;
   a lower end of the spring member is held by a spring holding member that holds a holder, one end of which is held by the bottom surface portion; and
   the spring member is a tension spring that urges the moving pulley substantially vertically downward.

9. The X-ray apparatus for rounds according to claim 4, wherein the holding unit further includes a hoist portion provided on an upper surface of the upper surface portion to hoist the holding unit vertically upward.

10. The X-ray apparatus for rounds according to claim 4, further comprising:
    an opening for maintenance provided in a side surface of the support column; and
    an elevating mechanism that raises and lowers the holding unit and is detachable from the support column via the opening.

* * * * *